United States Patent [19]

Heller

[11] Patent Number: 4,684,088

[45] Date of Patent: Aug. 4, 1987

[54] SUPPORT APPARATUS FOR AN OPTICAL OBSERVATION DEVICE

[75] Inventor: Rudolf Heller, Zürich, Switzerland

[73] Assignee: Contraves AG, Zürich, Switzerland

[21] Appl. No.: 855,918

[22] Filed: Apr. 25, 1986

[30] Foreign Application Priority Data

May 13, 1985 [CH] Switzerland ............... 2032/85

[51] Int. Cl.⁴ ............................................ A47G 29/00
[52] U.S. Cl. .................................. 248/123.1; 74/103; 248/280.1; 414/917
[58] Field of Search ............ 248/123.1, 280.1, 281.1, 248/122, 124; 901/15; 414/917, 749; 74/103

[56] References Cited

U.S. PATENT DOCUMENTS

| | | | |
|---|---|---|---|
| 1,589,727 | 6/1926 | Travell | 74/103 |
| 2,683,481 | 7/1954 | Lorenz | 74/103 X |
| 4,335,315 | 6/1982 | Waerve et al. | 248/281.1 X |
| 4,344,595 | 8/1982 | Heller et al. | 248/280.1 X |
| 4,364,535 | 12/1982 | Itoh et al. | 901/15 X |
| 4,437,635 | 3/1984 | Pham | 248/281.1 X |

FOREIGN PATENT DOCUMENTS 750431  5/1943  Fed. Rep. of Germany.
2124320  2/1984  United Kingdom.

OTHER PUBLICATIONS

Machine Design, vol. 22, No. 1, Jan. 1950, pp. 90-92, Cleveland U.S.; H. G. Conway: "Straight-line Linkages", FIGS. 2, 4-6.

Primary Examiner—J. Franklin Foss
Assistant Examiner—David L. Talbott
Attorney, Agent, or Firm—Werner W. Kleeman

[57] ABSTRACT

The support apparatus in the form of a stand possesses an arm component projecting transversely from a stand component. A surgical operating microscope is arranged at the end of the arm component. A guide linkage with a double scissors type carrier linkage whose movement is combined with an extension movement is provided for the displacement of the operating microscope in a direction transverse to the stand component. This extension movement is controlled by a control linkage in such a way that the upper end of the carrier linkage which carries the stand arm component moves along a straight line. There is thus no need for a counterweight for the transverse movement of the operating microscope over a surgical operating table. A first counterweight for the upwardly and downwardly directed swinging movement of the stand arm component is enclosed in a space saving manner within a housing of the stand component, conjointly with a substantial portion of the guide linkage. The connection between the arm component of the stand and the first counterweight is effected through linkages a predominant portion of which are likewise substantially accommodated within the housing.

10 Claims, 5 Drawing Figures

SUPPORT APPARATUS FOR AN OPTICAL OBSERVATION DEVICE

BACKGROUND OF THE INVENTION

The present invention broadly relates to a new and improved construction of a support apparatus for an optical observation device.

In its more specific aspects the present invention relates to a new and improved construction of a support apparatus for an adjustably arranged optical observation device with a stand component extending substantially upwards from a base component. Projecting transversely from this stand component there is an arm component at whose free end the optical observation device or other analogous equipment is arranged. The stand component for adjusting or positioning the optical observation device or other equipment possesses a guide linkage pivotable, in a direction transverse to the stand component.

Stands designed as support apparatuses of this type are known, for example, from the commonly assigned German Pat. No. 2,320,266 and the European Pat. No. 0,023,003, with which there is cognate the U.S. Pat. No. 4,344,595, granted Aug. 17, 1982. A component extending upwards from a pivot axis is formed by an arm of a two armed lever such that a stand arm component fastened at the free end of this arm is moved in a circular path and such that a counterweight is necessary on the counter-arm of the lever. For a horizontal movement of the equipment in this known stand construction, it is necessary to equalize the downwards movement within the circular path with an upwards pivotable movement of the stand arm component. Due to the lateral swing of the counter-arm with the counterweight in a direction opposite to the movement of the equipment, such stands require a relatively large space. Furthermore, weight compensation when interchanging the equipment for equipment of a different weight is tedious, since the position as well as the size of the counterweight have to be changed.

SUMMARY OF THE INVENTION

Therefore, with the foregoing in mind, it is a primary object of the present invention to provide a new and improved construction of a support apparatus for an optical observation device or the like and which does not exhibit the aforementioned drawbacks and shortcomings of the prior art constructions.

A further significant object of the present invention is to provide a new and improved construction of a support apparatus for scientific or other instrumentation which does not exhibit the aforementioned drawbacks and shortcomings of the prior art construction.

Yet a further important object of the present invention is to provide a new and improved construction of a support apparatus for an optical observation device which requires less space without a reduction in the range of movement of the observation device.

Another significant object of the present invention is to provide a new and improved construction of a support apparatus for an optical observation device, and which apparatus has a reduced total weight, and particularly reduced weight of the movable components, in comparison to prior art constructions and thus exhibits reduced inertia affecting the displacement movement.

Still another significant object of the present invention is to provide a new and improved construction of a support apparatus for equipment, such as an optical observation device, and which apparatus does not require an exchange or replacement of counterweights when exchanging such equipment for equipment of different weight.

Now in order to implement these and still further objects of the invention, which will become more readily apparent as the description proceeds, the support apparatus of the present invention for an optical observation device is manifested by the features that an upwards extending component of the guide linkage comprises a carrier linkage which, in dependence of its movement, can be changed in length by means of a control linkage comprising first and a second control links.

In other words the support apparatus of the present development is manifested by the features that it comprises a pedestal and a stand component extending upwards from the pedestal. An arm component extends transversely from the stand component and has a free end region and the device to be positioned is arranged at this free end region of the arm component. The stand component contains a pivotable guide linkage for adjusting the device in a direction transverse to the stand component. The pivotable guide linkage comprises a joint and a member upwardly directed from the joint and having an upper end. The arm component is arranged at the upper end of the guide linkage. The upwardly directed member of the guide linkage comprises a carrier linkage having a variable length, and said pivotable guide linkage including a control linkage for varying said variable length of the carrier linkage as a function of its movement.

In accordance with the invention, transverse displacement of the arm component of the stand can be achieved in a non-circularly-shaped and preferably straight path in which the movement is guided by means of the control linkage. The guide linkage needs no outwardly pivotable counter-arm with counterweight for this transverse displacement, so that the weight and the spatial requirements are correspondingly reduced. Consequently, a substantial portion of the guide linkage and especially its control linkage can be enclosed in the housing associated with the support stand component. Thus, the portion of the stand so enclosed, because of reduced surface area requiring finish treatment, is less expensive to manufacture and the expenses of later servicing and cleaning work are reduced. This is of particular importance for use in clinical areas.

BRIEF DESCRIPTION OF THE DRAWINGS

The invention will be better understood and objects other than those set forth above will become apparent when consideration is given to the following detailed description thereof. Such description makes reference to the annexed drawings wherein throughout the various figures of the drawings there have been generally used the same reference characters to denote the same or analogous components and wherein.

DETAILED DESCRIPTION OF THE PREFERRED EMBODIMENTS

Figure 1:
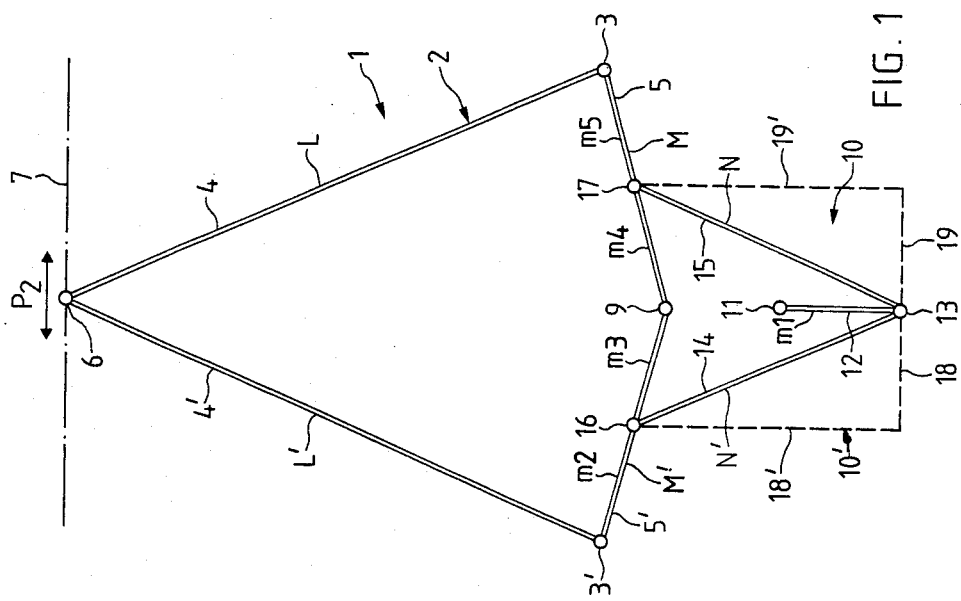
FIG. 1 shows a schematic depiction of a guide linkage for the displacement of the arm component transversely to the stand portion of a support apparatus in a starting position and depicted in greater detail in FIG. 4.

Describing now the drawings, it is to be understood that to simplify the showing thereof, only enough of the structure of the support apparatus for an optical observation device has been illustrated therein as is needed to enable one skilled in the art to readily understand the underlying principles and concepts of the present invention. Turning now specifically to FIG. 1 of the drawings, the support apparatus illustrated therein by way of example and not limitation will be seen to comprise a guide linkage designated in its entirety with the reference numeral 1. The guide linkage 1 comprises a double-scissored four-component or four-member carrier linkage 2 with respective first and second members or rods 4 and 4' and third and fourth members or rods 5 and 5' which are connected in pairs through first and second pivots or joints 3 and 3'.

An arm component 50 of the stand (not visible in FIG. 1 but shown in FIG. 4) is suitably pivotally arranged at a third pivot or joint 6 common to the upper ends of the first and the second rods 4 and 4' and can be guided by the guide linkage 1 along a line 7 in the direction indicated by double-headed arrow P2. The lower, and shorter, third and fourth rods 5 and 5' of the carrier linkage 2 are mounted on the first and second pivots 3 and 3' as well as at a fourth pivot 9. The carrier linkage 2 can be continuously altered in its length in accordance with the altered distance between the fourth pivot or joint 9 and a point on the line 7 at which the third pivot or joint 6 is situated, in order that the third pivot or joint 6, which carries the arm component of the stand, not move in a circular path when the guide linkage 1 pivots, but rather follows the line 7 in a substantially straight path. This alteration in the length is achieved in that the first to fourth rods 4, 4', 5 and 5' are correspondingly controlled or guided by a jointed first control linkage 10 and, as shown in FIG. 2, alter their mutually relative angular position with respect to each other.

The first control linkage 10 possesses a crank 12 linked to a stationary fifth pivot or joint 11 and the free end of the crank 12 is formed as a sixth pivot or joint 13. A first control member or rod 14 and a second control member or rod 15 form a connection between the sixth pivot or joint 13 and the associated third and fourth rods 5 and 5' of the carrier linkage 2 and are mounted at seventh and eighth pivots or joints 16 and 17.

The dimensional values or units in FIG. 1 designated by the reference characters m1 to m5 refer to a first length relationship of the individual rods, the reference characters L and L' to a second, the reference characters M to and M' to a third and the reference characters N and N' refer to a fourth. The not particularly referenced distance between the fourth pivot or joint 9 and the fifth pivot or joint 11 is substantially equal to the first length m1 of the crank 12, i.e. the distance between the pivots or joints 11 and 13, and the first distances m3 and m4 between the fourth pivot or joint 9 and the seventh and eighth pivots or joints 16 and 17 of the first and second control rods 14 and 15 at the third and fourth rods 5 and 5' of the carrier linkage 2. The third lengths M and M' of the third and fourth rods 5 and 5' are equal to twice the first distances m1 to m5, whereas the fourth lengths N and N' of the first and second control rods 14 and 15 are a multiple of 2.5, and the second distances L and L' of the first and second rods 4 and 4' of the carrier linkage 2 are a multiple of 5, of any of the first distances m1, m2, m3, m4 or m5. These lengths and distance relationships or spacings are preconditions for the guidance of the arm component 50 of the stand arranged at the third pivot or joint 6 along the straight line 7.

Figure 2:
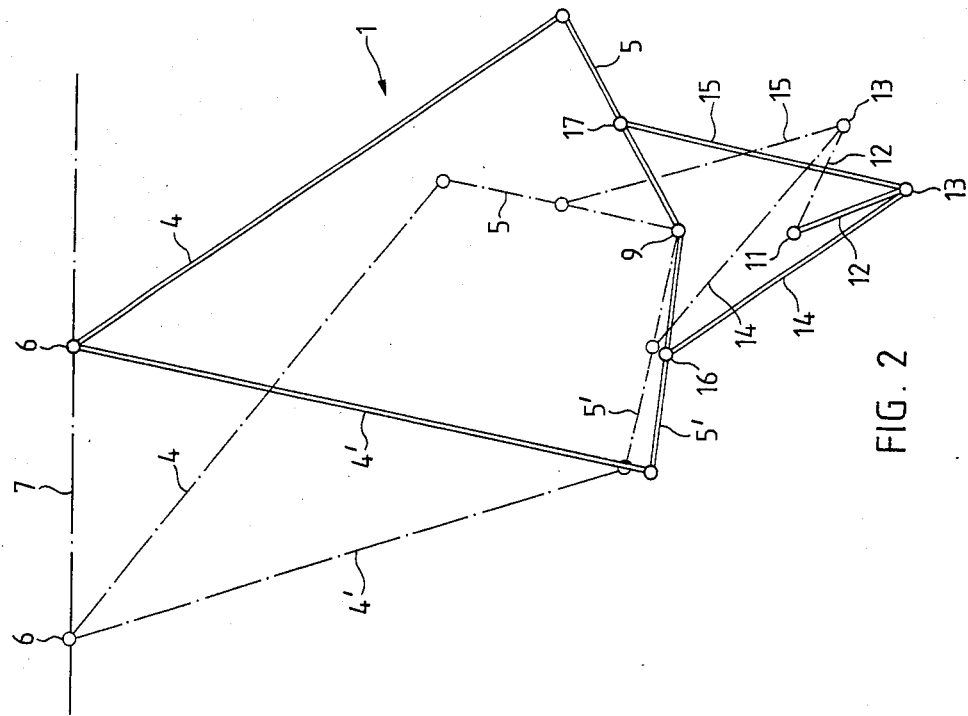
FIG. 2 shows the guide linkage in accordance with FIG. 1 in various pivotable positions.

It should be self-evident that the individual members or rods of the guide linkage 1 need not comprise straight rods as schematically shown in FIGS. 1 and 2, since it is only essential that the parts or components form the connection between the above-mentioned pivots or joint components 3, 3', 6, 9, 11, 13, 16 and 17 at the above-mentioned distance relationships. For example, the first control rod 14 and the second control rod 15 can be replaced by an angled, bifurcated, second control linkage 10', as is shown in FIG. 1 by the dashed lines 18, 18', 19 and 19' as well as in the preferred exemplary embodiment in accordance with FIG. 4.

Figure 3:
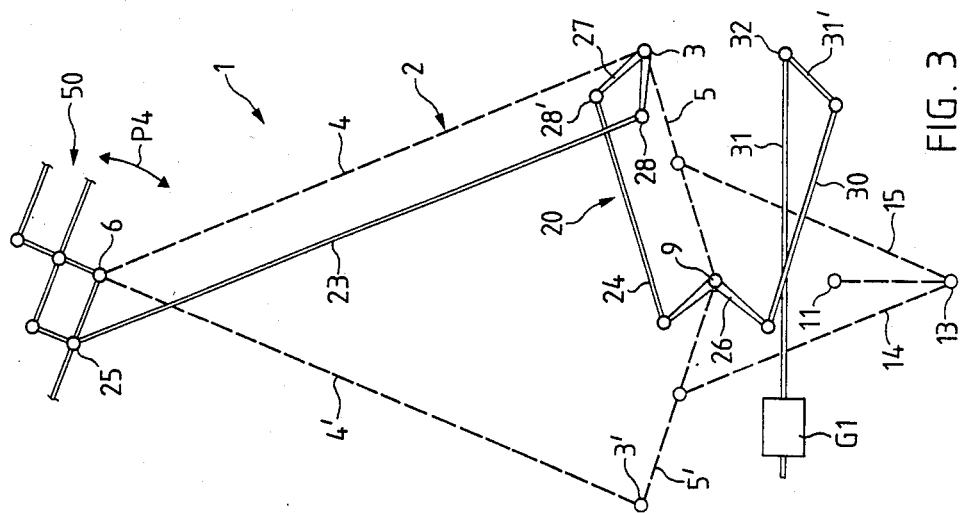
FIG. 3 shows a schematic depiction of a linkage for weight equalization for the upwardly and downwardly pivotable movement of the arm component of the support apparatus in accordance with FIGS. 1 and 4.

In accordance with the dashed lines of the guide linkage 1 in FIG. 3, a weight equalization linkage 20 is provided through which the connection between the arm component 50 of the stand and a correspondingly arranged first equalization or balance weight G2 is established for the weight equalization or compensation of the arm component 50 as it pivots upwardly and downwardly essentially about the third pivot or joint 6 in the direction of the arrow P4. The weight equalization linkage 20 possesses first and second links or rods 23 and 24 which are arranged parallel to the first and third rods 4 and 5, respectively, as shown in dashed line in FIG. 3, of the carrier linkage 2 and establish a ninth pivot position 25 and a connection between this ninth pivot position 25 and a first angled lever or bell crank linkage 26. The first angled lever or bell crank linkage 26 is mounted about the not here particularly shown axis of the fourth pivot 9. A second angled lever or bell crank linkage 27 is mounted about the axis of the first pivot or joint 3 which is in effective connection with the first and second links or rods 23 and 24 by means of tenth and eleventh pivots or joints 28 and 28'. This ensures conjoint movement of the weight equalization linkage 20 with the guide linkage 1.

A further or third connecting link 30 is in effective connection with the first angled lever or bell crank linkage 26 and with a fourth and fifth angled lever or bell crank linkage 31 and 31' mounted on a stationary twelfth pivot or joint 32. The first equalization weight G1 is displaceably mounted on the fourth angled lever or bell crank linkage 31. For an unhindered movement of the weight equalization linkage 20, which is shown in FIG. 3 in solid lines with the effectively connected components, this weight equalization linkage 20 is arranged, for example, in a vertical plane parallel to the plane of the guide linkage 1 shown in FIG. 3 in dashed lines.

Figure 5:
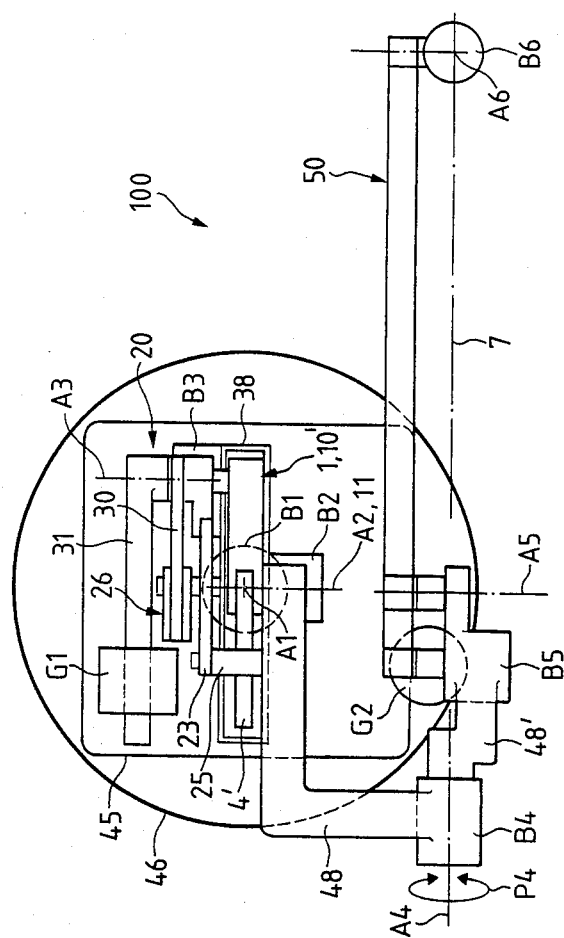
FIG. 5 shows a top plan view of the support apparatus depicted in FIG. 4.
Figure 4:
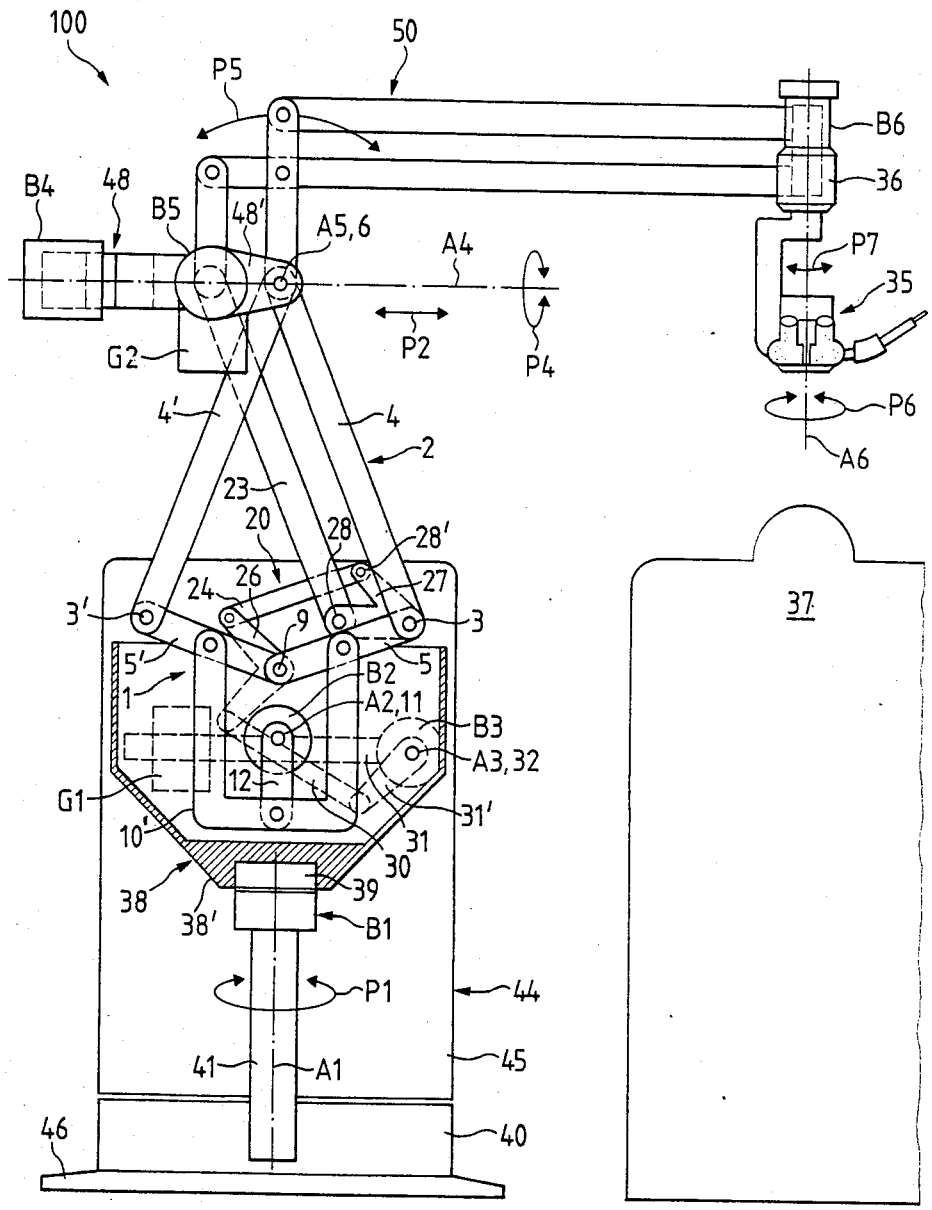
FIG. 4 shows a schematic sectional view of the support apparatus in accordance with the invention.

FIGS. 4 and 5 depict, in section and in a top plan view, a practical exemplary embodiment of a support apparatus 100 in the shape of a stand with integrated guide and control linkages 1 and 10 as well as the weight equalization linkage 20. The general use of the same reference numerals for the same components as in FIGS. 1 to 3 indicates which components or members of the support apparatus 100 generally correspond to the previously described components or members of the diagrammatic figures previously discussed so that repeated description is unnecessary.

The arm component 50 mounted and connected at the upper end of the guide linkage 1 formed as a parallelogram arm is essentially the same as is described in the hereinbefore recited European Pat. No. 0,023,003. In the region of the free end, a microscope E, for instance a surgical operating microscope 35, is pivotingly mounted on a head piece 36. It is the function of the support apparatus 100 to move this operating microscope 35 in all directions and to hold or support it in any desired position over a schematically depicted operating table 37 for which purpose six degrees of freedom, i.e. six axes of motion A1 to A6, are provided. Each degree of freedom of movement is achieved by means of a pivoting or turning motion of the individual elements about one of the first to sixth axes A1 to A6.

In order to be able to block or arrest the operating microscope 35 in a desired position and alignment after moving it, for example, by hand and in order to be able to keep it in this position, there are arranged for the turning and pivotable movements of the above-mentioned first to sixth axes A1 to A6 (as in the aforementioned known apparatuses) appropriate conventional magnetic rotation and braking bearings B1, B2, B3, B4, B5 and B6. The release of these magnetic braking bearings B1 to B6 by means of a not here particularly shown electrical switch arranged at the operating microscope 35 permits a positional and alignment alteration of the operating microscope 35 by applying a low force to overcome the friction of the rotation and braking bearings B1 to B6. The substantial effort required for overcoming inertial forces is very much reduced as a result of the elimination of an equalizing weight for the swinging motion of the guide linkage 1 which is rendered possible by the present invention. If desired, however, a relatively small second equalizing weight G2 can be provided by means of which the center of gravity of the system comprising the operating microscope 35, the parallelogram arm component 50 and the counterweight or equalizing weight G2 can be brought on to the line of motion 7. Then a displacement of the operating microscope 35 along the line of motion 7 which is essentially coincident with the fourth pivot axis A4 will generate no torque caused by inertia.

As can be seen in FIG. 4 a column 41 which defines the axis A1 is mounted in a pedestal or base component 40 in a not here further described manner. The first rotation and braking bearing B1 is arranged at the upper end of the column 41. The first rotation and braking bearing B1 has the purpose of rotatably supporting a housing-like frame 38 with a bearing mount 38' comprising a substantially circularly cylindrical head piece 39. The frame 38 serves for storing the guide and control linkages 1 and 10' as well as the weight equalization linkage 20. The guide linkage 1 and the second control linkage 10' is thus substantially arranged in the frame 38 and mounted about the second pivot axis A2 which is operatively associated with the second braking bearing B2. The weight equalization linkage 20 is mounted on the third pivot axis A3 which is operatively associated with the third braking bearing B3 and the fourth pivot or joint 9 of the guide linkage 1 and is laterally arranged on the frame 38.

The arm component 50 which is arranged at the upper region of the guide linkage 1 is mounted on first and second angular shaped carrying arms 48 and 48' and is rotatable in the direction of the arrow P4 about the fourth pivot axis A4, which is operatively associated with the fourth braking bearing B4. Furthermore, the arm component 50 swings in the direction of the arrow P5 about the fifth pivot axis A5, which is operatively associated with the fifth braking bearing B5. The operating microscope 35 arranged at the front end of the arm component 50 is rotatable in the direction of the arrow P6 about the sixth pivot axis A6, which is operatively associated with the sixth braking bearing B6 and is preferably mounted to swing within a limited region in the head piece 36 in the direction of the arrow P7.

A stand component 44, which is shown schematically in FIG. 4, possesses a housing 45 which is adapted in cross section to the pedestal or base component 40 and which surrounds the column 41 as well as the linkages 1 and 20 up to a level above the first and second pivots 3 and 3' and the tenth and eleventh pivots or joints 28 and 28'. The frame 38 which carries the linkages 1, 10' and 20, together with the arm component 50, is rotatable about the first pivot axis A1 in the direction of the arrow P1. The pedestal or base component 40 possesses an outwardly facing flat ring or annular shaped floor base plate 46 which serves for enhancing the stability of the support apparatus 100.

In FIG. 5 the support apparatus 100 is depicted schematically in a top plan view and there can be recognized the frame 38, arranged in the housing 45, with the guide linkage 1 and the second control linkage 10' mounted therein. There can also be recognized the weight equalization linkage 20 with the first equalizing weight G1 arranged at one side of the frame 38 as well as the arm component 50 arranged at the other side of the frame 38. The depiction of FIG. 5 further shows that the arm component 50 is arranged to be transversely displaced with respect to the first vertical axis A1 or, respectively, to the axis of the housing 45. The arm component 50 is held by the first and second angular shaped carrying arms 48 and 48' which essentially establish the connection with the guide linkage 1.

The adjustment of the position of the equalizing weight G1 on the fourth angled lever 31 for adapting to the weight of a different operating microscope or other equipment or device can be achieved by means of a suitable electric motor. A here not particularly shown drive can also be provided for the displacement of the guide linkage 1, that is, for carrying out the translation movement of the operating microscope. The torque of this motor could be applied to either one of the rods 5 or 5' or to the crank 12 of the guide linkage 1.

While there are shown and described present preferred embodiments of the invention, it is to be distinctly understood that the invention is not limited thereto, but may be otherwise variously embodied and practiced within the scope of the following claims. Accordingly,

What I claim is:

1. A support apparatus for adjustably positioning a device, comprising:
   a stand component;
   an arm component extending transversely relative to said stand component and having a free end region at which there is capable of being arranged the device;
   a pivotable guide linkage cooperating with said stand component for adjusting the device in a direction transverse to said stand component;

said pivotable guide linkage comprising a joint and a structure upwardly directed from said joint and having an upper end;

said arm component being arranged at said upper end of said pivotable guide linkage;

said upwardly directed structure of said guide linkage comprising a carrier linkage having a variable length; and said pivotable guide linkage further comprising a control linkage which is positioned below and in coacting relationship with said carrier linkage for varying said variable length of said carrier linkage as a function of its movement.

2. The support apparatus as defined in claim 1, wherein:

said carrier linkage comprises a double scissors carrier linkage;

said double scissors carrier linkage containing four rods; and said four rods being arranged in pairs and being interconnected by means of four related joints.

3. The apparatus as defined in claim 2, further including:

a crank having a pivot;
two pivot joints;
said four rods including a pair of rods;
said control linkage comprising first and second control linkages;

said first and second control linkages comprising a first control rod having a first end and a second end and a second control rod having a first end and a second end; and said first end of said first control rod and said first end of said second control rod being connected at said pivot of said crank and said second end of said first control rod and said second end of said second control rod being connected via said two pivot joints to said pair of rods of said carrier linkage.

4. The apparatus as defined in claim 3, further including:

a further pivot defining a pivot axis of said crank;
said first and second control rods being mounted conjointly with said crank at said further pivot joint; and said carrier linkage being arranged for pivoting conjointly with said first and second control rods.

5. The apparatus as defined in claim 4, wherein:
said crank has a predetermined length between said further pivot and said pivot of said crank;
said first control rod having a length 2.5 times as great as said predetermined length;
said second control rod having a length 2.5 times as great as said predetermined length;
said pair of rods of said four rods comprising a first rod and a second rod;
said first rod having a length twice as great as said predetermined length;
said second rod having a length twice as great as said predetermined length;
said four rods of said double scissors carrier linkage comprising a third rod and a fourth rod;
said third rod having a length five times as great as said predetermined length;
said fourth rod having a length five times as great as said predetermined length;

a predetermined one of said joints of said four related joints of said pivotable guide linkage being situated at a distance from said further pivot which is substantially equal to said predetermined length of said crank;

said predetermined one of said pivots defining said joint from which there is upwardly directed said structure of said pivotable guide linkage;

said first control rod being pivotably connected to said first rod of said pair of rods at a location remote from said predetermined joint of said pivotable guide linkage by a distance equal to said predetermined length of said crank; and said second control rod being pivotably connected to said second rod of said pair of rods at a location remote from said predetermined joint of said pivotable guide linkage by a distance equal to said predetermined length of said crank.

6. The apparatus as defined in claim 4, further including:

a column having an end and a substantially vertical pivot axis;

a frame rotatably mounted in said stand component at said end of said column about said substantially vertical pivot axis; and said further pivot defining said pivot axis of said crank being mounted within said frame.

7. The apparatus as defined in claim 6, further including:

an equalizing weight;
an equalization linkage possessing a pivot defining a pivot axis and carrying said equalizing weight;
said equalization linkage being operatively connected to said arm component and to said pivotable guide linkage;

said pivot axis of said equalization linkage being arranged substantially parallel to said pivot axis of said crank; and said equalizing weight being laterally arranged in relation to said frame for movement about said pivot axis of said equalization linkage.

8. The apparatus as defined in claim 1, wherein:
said stand component comprises a housing;
said pivotable guide linkage containing a predetermined portion thereof; and
said control linkage and said predetermined portion of said guide linkage being enclosed in said housing of said stand component.

9. The apparatus as defined in claim 1, further including:

a pedestal cooperating with said stand component;
a substantially flat, annular floor base plate; and
said floor base plate projecting outwards from said pedestal.

10. The apparatus as defined in claim 7, further including:

a further equalizing weight arranged in the region of said upper end of said structure of said pivotable guide linkage;

said arm component and the device to be positioned defining components of a system having a common center of gravity with said further equalizing weight; and said center of gravity of said system lying essentially on a common line of movement of said components of said system.

* * * * *

UNITED STATES PATENT AND TRADEMARK OFFICE
CERTIFICATE OF CORRECTION

PATENT NO. : 4,684,088

DATED : August 4, 1987

INVENTOR(S) : RUDOLF HELLER

It is certified that error appears in the above-identified patent and that said Letters Patent is hereby corrected as shown below:

Column 4, line 28, please change "G2" to --G1--

Signed and Sealed this

Sixteenth Day of February, 1988

Attest:

DONALD J. QUIGG

Attesting Officer

Commissioner of Patents and Trademarks